United States Patent [19]

Leong et al.

[11] Patent Number: 4,863,689

[45] Date of Patent: Sep. 5, 1989

[54] APPARATUS FOR THE DETECTION OF CHEMILUMINESCENCE

[75] Inventors: Merlin L. Leong; John S. Hayward; Glyn R. Fox, all of Victoria, Canada

[73] Assignee: University of Victoria, Canada

[21] Appl. No.: 126,857

[22] Filed: Nov. 30, 1987

[30] Foreign Application Priority Data

Apr. 23, 1987 [CA] Canada ................................. 535451

[51] Int. Cl.⁴ ..................... C12M 1/20; G01N 21/76; B01L 3/00
[52] U.S. Cl. ....................................... 422/52; 422/61; 422/68; 422/102; 435/8; 435/35; 435/291; 436/135; 436/172; 436/546
[58] Field of Search ..................... 422/52, 61, 68, 102, 422/104, 66; 23/230 R, 230 B; 435/8, 35, 291; 436/135, 172, 546

[56] References Cited

U.S. PATENT DOCUMENTS

| | | | |
|---|---|---|---|
| 2,865,744 | 12/1958 | Friedman et al. | 96/27 |
| 3,239,406 | 3/1966 | Coffman et al. | 161/167 |
| 3,795,489 | 3/1974 | Warnick et al. | 23/254 R |
| 3,801,324 | 4/1974 | Postal | 96/82 |
| 3,923,462 | 12/1975 | Cavanagh | 23/232 R |
| 4,181,650 | 1/1980 | Maier, Jr. | 260/112.7 |
| 4,231,754 | 11/1980 | Vogelhut | 422/52 |
| 4,396,579 | 8/1983 | Schroeder et al. | 422/52 |
| 4,429,050 | 1/1984 | Yasuda et al. | 436/538 |
| 4,543,308 | 9/1985 | Schumann et al. | 430/21 |

FOREIGN PATENT DOCUMENTS

| | | |
|---|---|---|
| 407671 | 9/1942 | Canada . |
| 1067740 | 12/1979 | Canada . |
| 1072387 | 2/1980 | Canada . |
| 1136467 | 11/1982 | Canada . |

Primary Examiner—Mukund J. Shah
Attorney, Agent, or Firm—Nixon & Vanderhye

[57] ABSTRACT

Apparatus is provided for the detection of chemiluminescence, e.g., the luminescent assay of an analyte in a sample. Sample, namely the production of a permanent photographic record of such chemiluminescence, e.g., by the use of a POLAROID film. The apparatus includes three interrelated elements. The first element comprises a film holder for holding a photographic film sensitive to a chemiluminescent reaction of the sample, the film holder defining a window in registry with any photographic film which may be held in the film holder. The second element comprises a sample holder for holding the sample in registry with the window and any photographic film which may be held in the film holder, and for allowing movements of the sample relative to any photographic film which may be held in the film holder between (i) a raised position, wherein the sample holder, and thus the sample is in spaced relation to any photographic film which may be held in the film holder and (ii) a lowered position, wherein said sample holder is in sufficiently close proximity to and photographic film which may be held in the film holder means to allow the sample held thereby directly to contact any photographic film which may be held in the film holder. The third element comprises a shutter operatively associated with the window of the film holder and movable between a closed position, wherein the shutter obstructs the window so as to prevent the sample holder from moving into the lowered position, and an opened position, wherein the window is unobstructed by the shutter so as to permit the sample holder to move from the raised position to the lowered position.

25 Claims, 2 Drawing Sheets

APPARATUS FOR THE DETECTION OF CHEMILUMINESCENCE

BACKGROUND OF THE INVENTION

1. Field of the Invention

This invention relates to a method and apparatus for the detection of chemiluminescence, e.g., the luminescent assay of an analyte in a sample. Preferably apparatus and methods are provided in the rapid production of a permanent photographic record of such chemiluminescent, e.g. by the use of a POLAROID film.

2. Description of the Prior Art

Luminescence may be simply defined as the emission of visible or invisible radiation which is the result of a chemical reaction. In chemiluminescence the source of the energy is a chemical reaction. A special form of chemiluminescence is bioluminescence, which is found in the biological systems, in which a catalytic protein increases the efficiency of the luminescent reaction.

Chemiluminescent reactions systems generally require an oxidant (for example, hydrogen peroxide); a catalyst, (for example microperoxidase, heme, hemoglobin or cobalt); and a chemilumingenic compound.

Large number of substances can be accurately determined by means of chemiluminescent reactions. Such reactions generate light, the intensity of which is directly proportional to the concentration of the reacting substances. If during the reaction the luminescent substance is in excess, the light intensity is directly proportional to the concentration of the substance investigated in the sample; thus a simple measurement of light intensity yields an accurate determination of the sample concentration. The radiation can be generated in any of the visible, ultraviolet and infrared spectral regions.

Conventionally, the known test systems have been of the type which include in the reagent composition one or more chromogenic redox indicators which are either directly responsive to the analyte to be determined, or are combined with and react to the product of an analyte responsive system. The known sensitivity of luminescence assays and their applicability to analytical intermediates, e.g. ATP, NAD(H) and peroxide, have led to the use both of chemiluminescence and bioluminescence as analytical tools in clinical chemistry.

Until recently, most luminescence measurements have been made by using individually constructed apparatus or commercial equipment modified to meet the peculiar requirements of luminescence. Commercially available instruments which have been modified include photometers, fluorometers and scintillation counters.

Another approach which has been taken in efforts to measure luminescence is the exposure of photographic film to light emitted by the luminescent reaction. Chemiluminescent reactions have been monitored on film to detect enhancers, inhibitors, catalysts and oxidants in various systems.

Another suggestion was to inject a sample and chemiluminescent reagents into a sealed container surrounded by photographic film and then measuring the film exposure as a function of concentration.

Moreover, other processes are known according to which a recording which has already been produced image-wise is converted into luminescence images by toning processes or by printing processes.

The patent literature is replete with patents relating to methods and apparatus for assays using chemiluminescence.

U.S. Pat. No. 2,865,744, patented Dec. 23, 1958, by J. S. Friedman et al. was directed to fluorescence in photographic emulsions and to a duplicating process using such fluorescence. The patentee provided a process of preparing a direct duplicate from a transparent original by exposing with blue light through the original, a photographic material carrying, on a transparent support, a silver halide emulsion containing a sensitizing dye capable of increasing the fluorescence of the emulsion, for a specified period of time. Then the process involved exposing with blue light through the exposed intermediate printing material, a duplicating material carrying, on a suitable support, a panchromatic emulsion while interposing a yellow filter between the intermediate and the duplicating material. The yellow filter absorbed all of the blue light but transmitted the fluorescent light emitted by the intermediate material to be recorded upon the panchromatic emulsion. The latent image in the duplicating material was developed in a black and white developer to form a duplicate picture of the original.

Coffman, U.S. Pat. No. 3,239,406, disclosed a chemiluminescent tape useful as a marker. Upon exposure to air, the tape chemiluminesced for different periods of time and at different levels of illumination depending upon the type and amount of chemiluminescent composition incorporated in the structure. The tape comprises at least one layer or surface which was adhesive to other surfaces and which had at least a surface impregnated with a chemiluminescent composition containing at least one peraminoethylene and a strippable film overcoat or removable envelope to protect the peraminoethylene composition from exposure to oxygen prior to use.

U.S. Pat. No. 3,795,489, patented Mar. 5, 1974 by A. Warrick et al, related to a chemiluminescence reaction chamber in which a gaseous sample mixture and gaseous reactant mixture were brought together at one edge of a shallow, disc-shaped, reaction chamber. The exhaust opening of the reaction chamber was located diametrically from the mixture inlet. A light-transmitting element formed one wall of the reaction chamber and the reacting gases passed through the reaction chamber in a plane substantially parallel to the light-transmitting element.

U.S. Pat. No. 3,801,324, patented Apr. 2, 1974, by H. R. Postal, was directed to a non-conflicting, double-image photographic film employing both silver-based and photofluorescer compounds. The invention resided in the provision of a photographic film element having photographic medium and optically-active medium for providing identifying indicia. The optically-active medium was a compound which was converted to a fluorescent state by short wave ultraviolet radiation and which could be read by longer wave ultraviolet.

U.S. Pat. No. 3,923,462, patented Dec. 2, 1975, by L. A. Cavanagh related to photographic detection and integration of light emitted from luminescent reactions. Cavanagh disclosed an automated apparatus for the detection of ozone in ambient air. A sample of air was passed through a light-tight enclosure where it reacted with a material, e.g. Rhodamine B, which luminesces in the presence of ozone, or a material which normally luminesces (e.g. in black light) and was quenched in the presence of ozone. Photographic film was positioned in the enclosure and was spaced apart from the chemiluminescent system. The film was in exposed relationship to the luminescent reaction inside of the light-tight enclosure.

U.S. Pat. No. 4,181,650, issued Jan. 1, 1980, to C. I. Maier, Jr., related to a method for the rapid, accurate, quantitative or qualitative determination of biologically-active substances at extremely low concentrations. The patentee provided a determination of the presence and amount of a specific organic substance (ligand) that will form a complex with a macromolecule (antibody) which could be made by means of a reagent obtained by binding a chemiluminescent substance to the ligand to be assayed. The addition of a limited amount of a substance (antibody) having receptors for the ligand together with the chemiluminescent-labeled ligand to the fluid to be assayed resulted in a competitive reaction between the ligand present in the fluid and the chemiluminescent-labeled ligand for the limited number of receptor sites. Under equilibrium conditions, the amount of chemiluminescent-labeled ligand bound to the antibody was related to the amount of unlabeled ligand in the solution being assayed, and was determined by isolating the antibody and measuring its chemiluminescence, or by isolating and measuring the amount of free labeled-ligand remaining.

U.S. Pat. No. 4,231,754, patented Nov. 4, 1980, by P. O. Vogelhut, related to a chemiluminescent analytical device. The patentee provided a test device for determining an analyte in a sample. The test device included a unitary solid carrier incorporated with a first reagent system responsive to the presence of the analyte to produce a reaction product. A second reagent system was responsive to the presence of that reaction product to produce luminescence. The test device was said optionally to include a photoresponsive layer physically associated with the carrier means and which was responsive to light produced by the chemiluminescent system.

U.S. Pat. No. 4,396,579, patented Aug. 2, 1983, by H. R. Schroeder et al, related to a luminescence detection device for quantitatively detecting an analyte in a liquid sample. The device included a compartment having, along a primary axis, opposite end portions, a first of which was for introduction of fluid reagents and sample into the compartment and the other of which formed a light-transmissive aperture of predetermined size, the compartment being suitable to hold a composition which luminesces in response to contact with analyte-containing sample. A closure was provided in the first end portion for admitting a cannula, so that fluid could be introduced into the compartment, and for closing the compartment. A photoresponsive, imaging layer was also provided, along with means for associating the photoresponsive imaging layer and the compartment such that the photoresponsive imaging layer was positioned, preferably substantially perpendicular to the primary axis of he compartment, at a predetermined distance from the end portion forming the aperture so as to be exposed to light emanating therefrom. Means were provided for preventing exposure of the photoresponsive image layer to ambient light. Light emitted from the aperture exposed a zone of the imaging layer which it contacted. The amount of light emitted was proportional to the amount of analyte in the sample. Even at low analyte concentrations, the light exposed a "base zone" of the imaging layer.

U.S. Pat. No. 4,429,060 patented Jan. 31, 1984, by Y. Uasuda et al, related to a competitive immunochemical measurement of plural trace components involving spectral sensitizing dye labels. The patented method included labeling an antigen or antibody with a spectral sensitizer having an absorption region of a wavelength longer than the intrinsic absorption wavelength of silver halide (preferably longer than 500 nm) which was adsorbed onto silver halide grains in order spectrally to sensitize the silver halide grains. The labelled substance was immunochemically reacted with an antibody or antigen. Either the reaction product of the unreacted antigen or the antibody was brought into contact with silver halide. The silver halide was exposed and developed. The quantity of the resulting developed silver or colored dye was then measured as optical density.

U.S. Pat. No. 4,543,308, patented Sept. 24, 1985, by H. J. Shumann et al, related to a photographic recording process. The patentee provided a technique for electronic image recording in one or more colors of a photographic recording material. The photographic material having, in at least one layer, photo-sensitive silver halide and a compound capable of luminescence was image-wise exposed and developed to produce a latent luminescence image. The image information contained in the latent luminescence image was scanned photoselectively by a luminescence spectroscopic process and was recoded electronically in the form of monochromatic luminescence signals.

Other patents of general interest include the following:

Canadian Pat. No. 475,984 which related to the concept of the use of a film, to detect substances present in small proportions in a carrier medium.

Canadian Pat. No. 1,067,740 which related to the concept of typing blood using a camera and a film, whereby the camera can take a composite image forming a photographic record of the typing results on a plate.

Canadian Pat. No. 1,072,387 which related to the concept of providing a movable sheet film holder for recording multiple images first appearing in a CRT tube.

Canadian Pat. No. 1,136,467 which related to the concept of providing a multi-image film cassette holder with automatic positioning for recording images originally appearing on a CRT tube.

SUMMARY OF THE INVENTION

Aims of the Invention

Current methods for detection of bioluminescence and chemiluminescence used in a pollution control and clinical applications as noted above, are based on the use of a reaction chamber where sample and reagents are introduced for reaction and luminescent emission, a photomultiplier or a film is used to detect luminescence, and a data recording unit records luminescence. These methods have limited resolution and sensitivity due to losses of light in transmission from the reaction chamber to the photo-detector, self-absorption of luminescence in the reaction chamber, and photodetector noise.

In spite of these patents there is still a need for a simple device and technique for the detection of even very minute amounts of a selected material or materials in a sample, i.e. to give a positive answer to the presence or absence of that selected material.

The above-identified U.S. Pat. No. 3,923,462 provided a system for detecting the presence of a given substance in a fluid and providing a means for indicating the amount of the substance present over a given time period. The patented method included the step of placing a photographic film in exposed relationship to a material which can undergo a luminescent reaction (either simulation or quenching) in the presence of a substance to be detected. A light-tight enclosure was provided around both the film and the material, and means were provided to introduce the fluid to be sampled in reacting relationship to the material so that a luminescent reaction could take place when the substance to be detected is present in the fluid sample. The photographic film was exposed by the luminescence and film exposure provided an indication of the intensity of illumination and the time during which the luminescent reaction has taken place. This was said to provide an indication of the total amount of the substance to be detected which was present during the time of exposure (an integrating function). However, this patent does not provide maximal analytical sensitivity since the photographic film is always positioned in spaced relation to the material which can undergo the luminescent reaction.

The above described U.S. Pat. No. 4,231,754 provided a device for determining an analyte in a sample. The device included a unitary solid carrier means incorporated with a first reagent system responsive to the presence of the analyte to produce a reaction product and a second reagent system responsive to the presence of the reaction product to produce luminescence. The test device could optionally also include a photoresponsive layer physically associated with the carrier means and responsive to light produced by the chemiluminescent system. However, this patent does not provide maximal analytical sensitivity due to the physical distance between the analyte and the photoresponsive layer.

The above described U.S. Pat. No. 4,396,579 does provide a luminescence detection device which employs simple, inexpensive components and allows a convenient quantitative visual read-out of luminescence for the detection of reaction components present at nanomolar concentrations. Measurements are said to be rapid and the image produced provided a permanent record. Luminescent assays, including immunoassays can be monitored on photographic film. This device, however, is designed for quantitative detection of an analyte. To accomplish this, the photographic imaging layer is placed at a specified distance from the reaction vessel by the use of a spacer. This allows the light from the reaction vessel to diffuse onto the imaging layer so that the diameter of the image is proportional to the analyte concentration. However, this device does not provide maximal analytical sensitivity due to the need to associate the photoresponsive imaging layer a predetermined distance from the aperture.

Thus an object of a broad aspect of this invention is the provision of an apparatus and method for the detection of chemiluminesce with maximal analytical sensitivity.

An object of another aspect of this invention is the provision of an apparatus and method for the luminescent assay of an analyte in a sample with maximal analytical sensitivity.

An object of yet another aspect of this invention is the provision of a method and apparatus for the instant photographic recording of chemiluminescence with maximal analytical sensitivity.

Statement of Invention

By the present invention, apparatus is provided for the detection of chemiluminescence and for the production of a permanent photographic record of such chemiluminescence. The apparatus comprises: (A) a first element comprising: (a) a sample holder including clamp means to hold a test sample in a transparent container in selected positions; and (b) holding means to hold such clamp means in a first position of such selected positions, where such transparent container containing such test sample is out of contact with such photographic film supply, and to release such clamp to a second position of such selected positions, where such transparent container containing such test sample is in direct contact with such photographic film supply; (B) a second element comprising: (c) a supply of photographic film sensitive to chemiluminescence; and (d) a shutter means to enable a source of chemiluminescence directly to contact a selected unit of such photographic film; and (C) a third element comprising: (e) an adaptor to provide a light-tight union between the first element (A) and the second element (B), such adaptor including a central window through which such sample holder projects; whereby, upon manual actuation of such holding means to release such sample clamp means, such sample holder is dropped, thereby to place such container containing such test sample into direct contact with such selected unit of photographic film.

This invention also provides apparatus for producing a permanent photographic record of a chemiluminescent reaction of a sample comprising: film holder means for holding a photographic film sensitive to a chemiluminescent reaction of such sample, such film holder means defining a window in registry with any photographic film which may be held in such film holder means; sample holding means for holding such sample in registry with such window and any photographic film which may be held in such film holder means, and for allowing movements of such sample relative to any photographic film which may be held in such film holder means between (i) a raised position, wherein such sample holding means, and thus such sample is in spaced relation to any photographic film which may be held in such film holder means, and (ii) a lowered position, wherein such sample holding means is in sufficiently close proximity to any photographic film which may be held in such film holder means to allow such sample held thereby directly to contact any photographic film which may be held in such film holder means; and shutter means operatively associated with the window of the film holder means and movable between a closed position, wherein the shutter means obstructs the window so as to prevent the sample holding means from moving into such lowered position, and an opened position, wherein the window is unobstructed by the shutter means so as to permit the sample holding means to move from such raised position to such lowered position. and (b) a shutter means to enable a source of chemiluminescence directly to contact a selected unit of the photographic film; (B) a second element comprising: (c) a sample holder including clamp means to hold a test sample in a transparent container in a selected position; and (d) holding means to retain such clamp means in a first position where the test sample in that container is out of contact with the film supply, and to release the clamp means to a second position where the test sample in that container is in direct contact with the film supply; and (C) a third element comprising: (e) an adaptor to provide a light-tight union between the first element (A) and the second element (B), the adaptor including a central open window to permit the holding means to release the clamp means to drop the sample holder to place the test sample in that container into direct contact with the photographic film.

By this invention, a method is also provided for the detection of chemiluminescence and for the production of a permanent photographic record of such chemiluminescence, the method comprising the steps of: (i) positioning a test sample in a transparent container out of contact with a supply of photographic film sensitive to chemiluminescence, the test sample and the film each being in a light-tight enclosure; (ii) initiating the production of a permanent record of chemiluminescent reaction by directly contacting the test sample in that container with the photographic film; (iii) after a predetermined period of time, stopping the production of that permanent record by moving the test sample in that container out of direct contact with the photographic film; and (iv) developing the photographic film, thereby providing a permanent photographic record of the chemiluminescent reaction.

OTHER FEATURES OF THE INVENTION

By a feature of the apparatus of this invention, the element (B) preferably comprises a box holding a plurality of units of prepackaged, instant-developing photographic film, so that the apparatus provides instant photodetection of chemiluminescence and the rapid production of permanent photographic record thereof. The shutter which is manually actuatable means preferably comprises a sliding shutter to provide an open central window to permit the holding means to release the clamp means to drop the sample holder to place that container containing the test sample into contact with a selected unit of photographic film.

By another feature of the apparatus of this invention, the sample clamp preferably comprises a box having an open bottom floor, and holding means to hold the test sample in that container therein. The test sample in a reactant container may be in the form of a sample sheet protected within a transparent sample container, e.g. a nitrocellulose membrane having the luminescent analyte absorbed thereon protected within a polyethylene bag. Alternatively, the test sample in that reactant container may be in the form of a plurality of well plates or tubes containing the luminescent liquid analyte.

By a feature of the apparatus of this invention, it is preferred that the inner face of the sample clamp be provided with a light-reflective surface.

By a feature of the apparatus of this invention, the sample clamp preferably is held to the sample holder by a holding means in the form of a lockable position adjuster held in an elevated position against the urging of spring means, e.g. a leaf spring. The position adjuster preferably is adapted to be unlocked to release the sample clamp to allow the sample clamp to be positively urged downwardly by the spring means, thus urging the test sample in that container into direct contact with the photographic film.

By a feature of the apparatus of this invention, the third element (C) provides a light tight union between the film holder and the sample holder, and preferably is of the type including cooperating tongues and grooves so that element (A) may slide with respect to element (B), or hinges and clamps without prejudice.

GENERAL DESCRIPTION OF THE EMBODIMENT OF THE APPARATUS OF THIS INVENTION

In one embodiment, the apparatus includes an adjustable sample holder which enables the test sample in the transparent container to be placed in direct contact with the photographic film after the shutter is opened. The test sample in that transparent container can then be withdrawn after exposure of the photographic film, and the shutter can be closed to protect the film from exposure to ambient light during processing. The test sample in that transparent container is preferably in a form in which an analyte is adsorbed onto a solid-phase, membranous matrix (e.g. a nitrocellulose membrane). The test sample in that transparent container may alternatively be in the form of liquid samples contained in transparent reaction vessels. As noted above, to initiate the test, the test sample in that transparent container is placed in direct contact with the photographic imaging layer, thereby providing maximal analytical sensitivity. During the test, exposure to ambient light is prevented.

BRIEF DESCRIPTION OF THE DRAWINGS

In the accompanying drawings.

DESCRIPTION OF PREFERRED EMBODIMENTS

Figure 1:
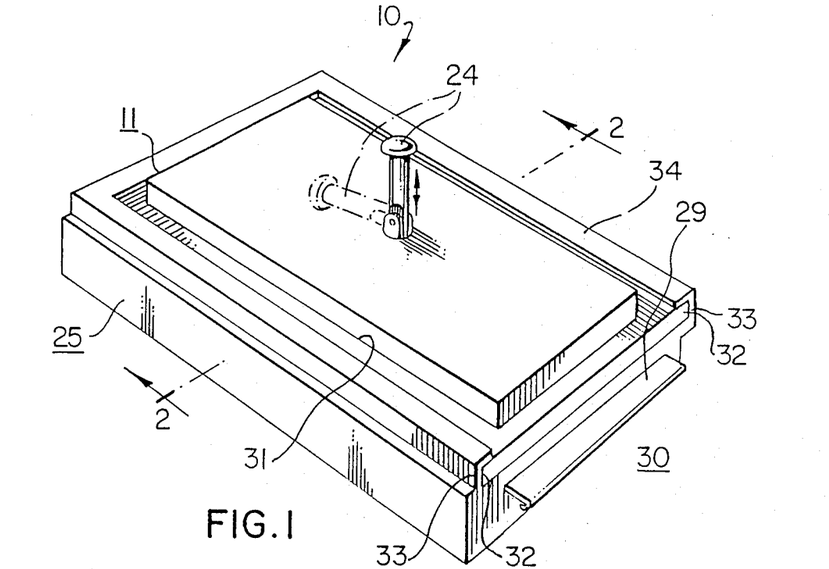
FIG. 1 is a cutaway perspective view of the test apparatus of one embodiment of this invention.

Description of FIG. 1

As seen in FIG. 1, the test apparatus 10 includes, as a first element, a sample holder 11, as a second element, a film holder 25, and as a third element, an adaptor 30. The sample holder includes a vertically-adjustable position adjuster in the form of a toggle bar 24, the bottom end of which is operatively associated in a manner to be described in greater detail hereinafter to a sample clamp (not seen in FIG. 1). When the toggle bar 24 is in the position shown by solid lines, the sample clamp can move vertically upwardly and downwardly. When the toggle bar is in the position shown by phantom lines, the sample clamp is retained in its upper, locked position.

The sample holder 11 is held to the film holder 25 in a light-tight manner by means of an adaptor 30. Adaptor 30 includes a rectangular window 31 through which the sample holder 11 projects and which enables sample clamp 15 to move upwardly and downwardly within fixed limits. The lateral edges 32 of the adaptor 30 slide within lateral grooves 33 of the film holder, and is prevented from upward movement by peripheral lip 34.

Figure 2:
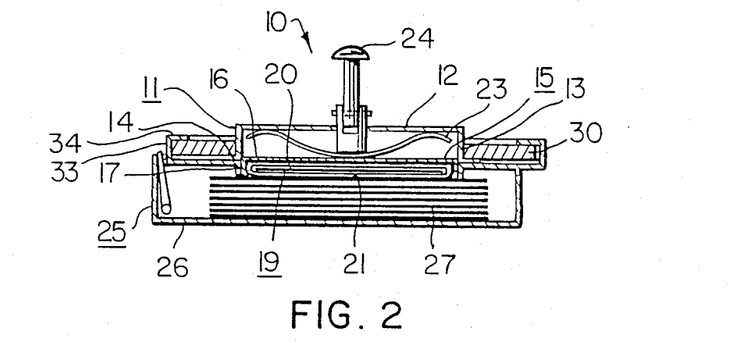
FIG. 2 is a schematic vertical cross-sectional view of the embodiment of the test apparatus of the present invention shown along line 2—2 of FIG. 1, but in its production of the permanent photographic record mode.
Figure 3:
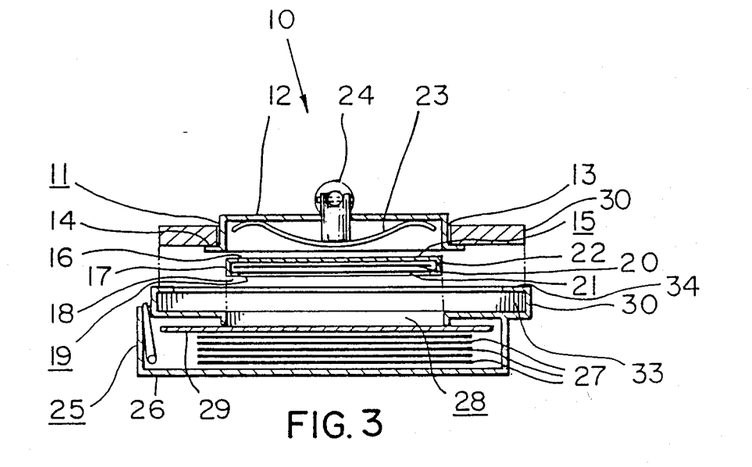
FIG. 3 is a schematic exploded cross-sectional view of the embodiment of the test apparatus of this invention, shown in FIG. 1.

Description of FIGS. 2 and 3

As seen in FIGS. 2 and 3, the sample holder 11 is in the form of a generally rectangular plate 12 having peripheral depending walls 13 terminating in an outwardly projecting flange 14. The sample holder 11 holds a sample clamp 15 in the form of a rectangular plate 16 having downwardly projecting peripheral walls 17 and inwardly directed flanges 18 to provide a rectangular window 19. Within sample clamp 15 is a test sample in a transparent reactant container. The test sample is in the form of a sample sheet 20 having the analyte absorbed thereon, the sheet 20 being protected within a transparent sample container 21, e.g. a polyethylene bag. The inside face of plate 16 is provided with a light reflecting surface 22.

Sample clamp 15 is abutted by leaf spring 23. Leaf spring 23 is secured to the lower end of toggle bar 24 so that it may be controllably urged against the upper face of plate 16 when toggle bar 24 is locked and so that it may urge sample clamp 15 downwardly when toggle bar 24 is unlocked.

Film holder 25 is in the form of a box 26 holding a plurality of units of prepackaged instant-developing film 27, e.g. that known by the Trade Mark POLAROID. The film holder is provided with a central window 28 and a conventional slidable shutter 29, which, when slid, opens window 28.

Adapter 30 provides a light-tight union of the first and second elements. As described with reference to FIG. 1, the lateral edges 32 of adaptor 30 slide within grooves 33 of film holder 25, and is prevented from moving upwardly by peripheral lip 34.

Figure 4:
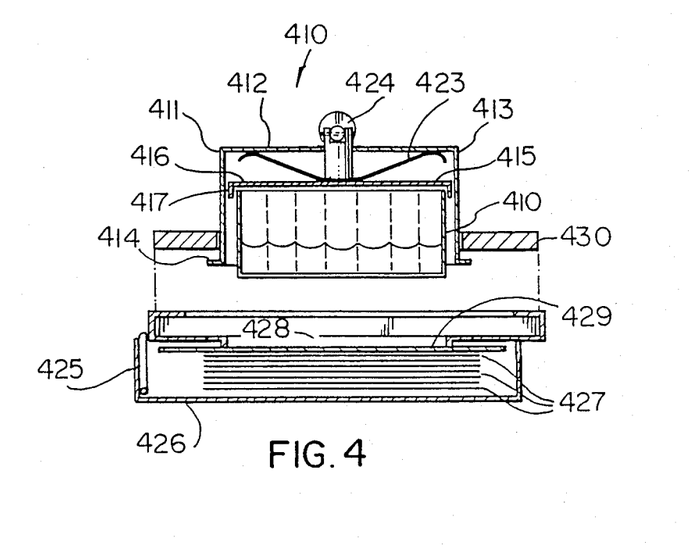
FIG. 4 is a schematic exploded view of another embodiment of the test apparatus of this invention.

Description of FIG. 4

The embodiment of FIG. 4 is generally the same as that in FIG. 1 and, where elements are the same as in FIG. 1, they will be given a reference number in the "400" series, i.e. the test apparatus of FIG. 4 is given reference number 410.

The only differences is in the test sample which is in the transparent reactant container contained in the sample clamp 415. The test sample which is in the transparent container is in the form of a plurality of well plates or tubes 420 containing liquid analyte.

OPERATION OF PREFERRED EMBODIMENTS

Use of Apparatus of FIG. 1

One example of the operation of an aspect of the invention is given in the operation of the device of FIG. 1. The test sample in a reactant container is in the form of a nitrocellulose membrane with luminescent samples, placed within a thin, transparent, waterproof container (e.g. a polyethylene bag, known by the Trade Mark ZIP-LOCK) to avoid desiccation. This test sample in that container is put in the sample holder by placement in the sample clamp. This clamp has a reflective surface for directing light outward from the sample holder in order to minimize light loss due to backscatter. The position adjuster is then withdrawn against spring pressure to retract the sample clamp within the holder and the samle clamp is locked in this position. The adapter can be of various designs (cooperating, sliding tongues and grooves, hinges, clamps, etc.) as long as a simple and light-proof connection is made.

The device is now ready for exposure of the photographic film. The shutter of the film holder is opened and the position adjuster is unlocked to allow the spring pressure to urge the sample clamp downwardly, so as to allow the sample container to pass through the opening of the adapter and to allow the test sample in the container to make direct contact with the photographic film. This event initiates timing of the exposure. At the end of the desired exposure, the sample container is withdrawn from the photographic film surface by retraction of the sample clamp, locking of the position adjuster, and closing of the shutter. The film can then be developed and fixed quickly using the POLAROID system. The end result is a permanent contact-print of the luminscence of the sample.

Experimental Embodiment

One experiment was carried out to determine the presence of IgE in non-immune human serum. A single nitrocellulose strip was spotted with 2 $\mu$l samples of non-immune human serum diluted to 1/712 with phosphate buffered saline. This was allowed to air dry and then was blocked for 1 hour in centrifuged milk. It was then spotted with 1 $\mu$l of biotinylated rabbit anti human IgE and incubated for 30 minutes. It was then washed twice with 100 ml of centrifuged milk containing 0.05% of a surface active agent known by the trade mark TWEEN 20. The nitrocellulose strip was then spotted with 2 $\mu$l of avidin-peroxidase (diluted 1/10 in phosphate-buffered saline), incubated for 30 minutes, and washed as described previously. The results were visualized using the light emitting substrate, luminol, the apparatus of embodiments of this invention, and film known by the trade mark POLAROID 667.

Depending on the time of exposure, a wide spectrum of detection was provided on the photographic film. Not only can the test be qualitative, but it can also be made quantitative by comparing the detected intensity. It is then possible to distinguish between a real reading and a false reading and to tailor-make the test to the assay.

VARIATIONS OF THE INVENTION

Modified Apparatus

It is possible to modify the apparatus to replace the adapter with a focusing lens. This would permit reduction of the light image from a very large sample holder (which would not require a position adjuster) onto a smaller film size. However the essence of the invention, the direct contact of the test sample in a reactant container with the photographic film must also be provided.

Modified Processes

The method of one aspect of this invention could involve the use of a luminescent substrate, luminol (5-amino-2,3-dihydro-1,4-phthalazinedione) for the detection of specific antibody-antigen complexes. Variable light emission of the reactants gives increased sensitivity of detection over chromogen-based assays. The use of specialized, high-speed film, which may be packaged for "instant" development and fixation, yields a permanent record simply, quickly, and inexpensively. The light-emitting sample or samples can be in bulk-liquid form (e.g. in transparent tubes or well-plates) or absorbed on solid supports (e.g. on a nitrocellulose membrane).

The present invention has referred generally to the detection of chemiluminescent reactions. For the sake of a complete disclosure of the broad scope of the present invention, the following discussion of chemiluminescent reactions is provided, all of which may be detected through the use of the method and apparatus of aspects of this invention.

The present invention may be used to detect and assay extremly small amounts (in the order of about 5-25 ng/ml) of a wide range of organic compounds in body fluids.

The assays, generally, will be conducted at moderate conditions of temperature, ranging from about 10° to about 50° C., at a pH in the range of about 5 to about 10, most often from about 6 to about 9. The manner of detecting the activity of the chemiluminescent assay consists of the direct detection of the chemiluminescent reaction by measuring the visible light emitted using the method and apparatus of aspects of this invention.

Those materials of a biological, biochemical or pharmacological nature, which may be assayed using the apparatus and method of aspects of the present invention, include many types of molecules including simple molecules, e.g. the phenyalkylamines, notably amphetamine, and the barbiturates, and those molecules possessing a high order of complexity, e.g. proteins, and suitably labeled nuclei acids.

Representative of the molecules which may be assayed using the apparatus and method of aspects of this invention, include:

Class I Drugs, their metabolites or derivatives and analogs. This class includes the alkoloids, e.g. opiates, e.g. morphine, heroin and other compounds of similar composition, as well as the analogs of these drugs, meperidine and its analogs, catecholamines; barbiturates; gluethimide; cocaine and its metabolites and analogs; diphenyldantoin; marijuana, tranquilizers, e.g. meprobamate, the benzdiazocycloheptanes, phenothiazines, etc.

Class II Amino Acids, polypeptides and proteins including: proteins, e.g. hemoglobin; enzymes; myoglobin, antibodies and immune response components; hormones, e.g. adrenocorticotrophic hormone (ACTH), oxytocin, luteinizing hormone, insulin, chorionic gonalotropin, pituitary gonadotropin, growth hormone, renin bradykinin, angiotensin, follicle stimulating hormone, and thyroxine binding globuline, thyroxine, and triiodothyronine.

Class III Steroids, which include: estrogens, gestrogens, androgens, adrenocortical hormones, bile acids cardiotonic glycosides, aglycones, and saponins, specifically testosterone, androsterone, equilenin, estrone, estriol, progesterone, pregnenolone, 17-hydroxydeoxycorticosterone, cortisol, aldosterone, digitoxin, digoxin, digoaigenin, and digitoxigenin.

Class IV Vitamins, representing a group of compounds, including: vitamin A, the B vitamin group, the D vitamins, vitamins E and K; the antibiotics, e.g. penicillin, tetracycline, actinomycin, nucleic acids, polynucleotides, nucleosides, serotonin 3-(2 aminoethyl)-5-hydroxyindole, spermine, galactose; phenylpyruvic acid; pesticides, fungicides; nematocides; cells, living or non-living, derived from varius sources, including bacterial, protosoan, plant fungal, vertebrate and nonvertebrate sources; viruses and viral particles; portions or extracts derived from cells, viruses; biological products derived as a consequence of or indicative of a specific physiologic condition or variety of conditions, e.g. alpha-feto-protein, carcinoembryonic antigen, and Dane Cores.

Several different chemiluminescent systems are known in the art, and the following are examples:

Strong chemiluminescence is obtained from cyclic diacyhydrazides, e.g. luminol (5-amino-2,3-dihydro-1,4-phthalizinedione) and isoluminol (6-amino-2,3-dihydrophthalazine-7,4-dione).

Annealated analogs of luminol have been found which are even more efficient at light production than luminol. One example is a compound having the formula:

Other chemiluminescent substances include tetrabis(-dimethylamino)ethylene, luciferin (of bacterial or firefly origin), lucigenin (dimethyl diacridinium nitrate), and oxalyl chloride. Also useful are the 2,3-dihydride phthalazine-1,4-diones.

With respect to the use of luminol, the efficiency, wavelength, and pH optimum of light emission in luminol depend greatly on reaction conditions. In general, hydrogen peroxide is the most commonly used oxidant; catalysts include $Fe(CN_6)^{3+}$ and $Cu^{2+}$. Other oxidants used include hypochlorite, iodine, permanganate, and oxygen in the presence of a suitable catalyst. One efficient catalyst in this reaction is heme, and one medium a carbonate buffer. The optimum pH for chemiluminescence varies somewhat with the catalyst and oxidant, but that for most oxidizing systems is near pH 11. The detection limit for luminol with the hydrogen peroxide/microperoxidase system is 1 picomol/liter.

With respect to the use of lucigenin (bis-N-methylacridinium nitrate), it is known that lucigenin luminesces on oxidation by peroxide in basic solution in the presence of metal ion catalysts. The reaction is catalyzed by some metal ions, e.g. $Pb^{2+}$, that do not catalyze the luminol reaction.

Other chemiluminescent assay systems which can be used in aspects of the present invention include:

Diaryl oxalates, e.g. bis(trichlorophenyl)oxalate which undergo a chemiluminescent oxidation reaction with hydrogen peroxide by way of a peroxyoxalate intermediate;

Bis(trichlorophenyl) oxalate in a ethyl acetate/methanol/aqueous buffer (pH range about 4–10) system containing triethylamine, for the analysis of peroxide, including the use of a fluoroscent molecule, perylene, as the light emitter because of its stability and its favorable efficiency and wavelength range of emission;

Lophine, which is oxidized in alkaline pH to give a yellow chemiluminescence;

Siloxane, which is oxidized in acidic pH to give a yellow-red chemiluminescence; and Polyhydric phenols e.g. pyrogallol and gallic acid.

The luminescent activity of a luminol-IgG conjugate is unaffected when bound to an antibody. In contrast, the luminescent activity of an isoluminol-biotin conjugate increases 10-fold when bound to avidin, a binding protein specific for biotin. This enhancement in light output has been ascribed to increased chemiluminescent efficiency mediated by the protein. Also a heterogeneous competitive binding immunoassay for thyroxine (T4) monitored by chemiluminescence uses a thyroxine label conjugate.

The chemiluminscent material may be attached or bonded either directly to the analyte, or through a suitable coupling agent which may function as a means of attachment of the chemiluminescent substance to the ligand. A suitable coupling agent is one which does not adversely affect the ultimate chemiluminescent and biochemical properties of the labeled ligand.

The functional group which is used to conjugate the chemiluminescent substance is, in the case of luminol, the amino group. In other compounds, e.g. luciferin, conjugation occurs through the hydroxy group. In general, chemiluminescent substances that have an amino group or carboxyl group form more stable conjugates with the molecule being assayed. It is also possible to modify the functional group of a chemiluminescent substance to provide for more stable binding to the ligand without adversely affecting its chemiluminescent activity.

The linking group that may be employed for the conjugation of the chemiluminescent molecule to the ligand may vary in size from one to thirty atoms, and may include one or several of the atoms of carbon, nitrogen, phosphorous, hydrogen, sulfur and oxygen.

As one illustration of the conjugation reaction, 5-amino-2,3-dihydro-1,4-phthalazinedione, (luminol) may be bound through the amino group. Direct conjugation of the luminol molecule may be accomplished by a variety of methods, for example, by reaction of the amino group of the luminol with thionyl chloride, with the formation of the isothiocyanate derivative, and the subsequent addition of the molecule being assayed possessing a reactive amino group, resulting in the formation of the thiourea derivative.

In the specific case where the analyte possesses a keto group, this group may be condensed with the amino group of the luminol, by treatment of the ligand with O-carboxymethyl hydroxylamine to form the carboxy methyl oxime derivative.

If a carboxyl group is present in the analyte, it may prove convenient to couple the analyte directly with the luminol molecule by the use of a suitable reagent, e.g. N-ethyl-3-dimethylamino-propyl carbodiimide or 1-cyclo-3-(2-morpholinoethyl)-carbodiimide. Addition of the carbodiimide reagent to the analyte, possessing the carboxyl group, results in the formation of the O-acylisourea derivative, which will react with the amino group of the luminol to effect conjugation. Alternatively, N-ethyl-5-phenylisoxazolium-3 sulfonate (Woodward's Reagent K) may be used for the direct conjugation of the analyte with the luminol.

The presence of hydroxyl groups, as in the case of sugars or their derivatives, may permit the use of a reagent, e.g. cyanogen bromide, for the conjugation. Sugar will react with cyanogen bromide, under appropriate conditions of pH, to form the imidocarbonate, which will react with luminol, to produce either the N-substituted imidocarbonate or an N-substituted carbamate.

An alternative procedure for the coupling of the analyte to the luminol, in those situations where the analyte possesses hydroxyl groups, as in the case of sugars, is the use of cyanuric chloride (2,4,6-trichloro-1,3,5-triazine) or other appropriate triazine derivatives, e.g. 2-amino-4,6-dichloro-5-triazine. A triazinyl derivative of the sugar is the first phase of this reaction, followed by the addition and attachment of the luminol molecule through its amino group.

Various bifunctional reagents e.g. glutaraldehyde, may also be employed for the conjugation of a chemiluminescent substance e.g. luminol, to the analyte. Under the appropriate conditions of pH and concentration, addition of the luminol to the amino group of the analyte occurs with at least one glutaraldehyde molecule functioning as a carrier or bridge as well as a linking agent.

A variety of activators may be used, alone or together to elicit the chemiluminescent activity. Suitable activators include the following:
 1. Hydrogen peroxide ($H_2O_2$);
 2. Hypochlorite (OCl)
 3. Sodium hydroxide (NaOH);
 4. Metals, e.g. iron ($Fe^{+3}$), Nickel ($Ni^{+2}$), cobalt ($Co^{+2}$)
 5. Iron-containing structures, e.g. the porphyrins and related structures (hemoglobin, cytochromes, myoglobin);
 6. polyvinylpyrrolidone;
 7. Riboflavin; and
 8. Ammonium persulfate.

Another reagent system for use in aspects of this invention is an enzyme which is characteristically an oxidase, e.g. glucose oxidase or cholesterol oxidase, which forms a oxidant, namely a peroxidatively active substance, e.g. hydrogen peroxide, periodate, ferricyanide or permanganate. Other oxidants include the peroxidases.

The peroxidases are generally conjugated proteins containing iron porphyrin. Peroxidase occurs in horseradish, potatoes, figtree sap and turnips (plant peroxidase); in milk (lacto peroxidase); in white blood corpuscles (verdo peroxidase), in microorganisms; and may be produced by fermentation. Peroxidatively-active substances are enzyme-like in that they catalyze the reduction of peroxides. Hemoglobin and its derivatives are typical of such "peroxidatively-active" substances because they behave in a manner similar to the behaviour of the enzyme peroxidase. Other substances which are not enzymes but which demonstrate peroxidative activity are: iron sulfocyanate, iron tannate, ferrous ferrocyanide, and chromic salts (e.g. potassium chromic sulfate) absorbed in silica gel.

Luminescent assays for enzymes, e.g. peroxidase (POD) are considerably more sensitive than are conventional colorimetric assays, a factor that has been exploited in the quantitation of enzyme conjugates in enzyme immunoassays. A luminescent enzyme immunoassay for cortisol involving luminescent quantitation of a peroxidase-cortisol conjugate has a sensitivity comparable with that of the radioimmunoassay.

Enzymic methods have been proposed for monitoring specific binding reactions, using ligand-cofactor (cofactor=CF) conjugates. The ligand has, for example, been covalently coupled to an enzymatically active derivative of NAD. After reduction with alcohol dehydrogenase and ethanol, these conjugates can be measured quantitatively by means of light production by using the bacterial luciferase system. The light production of ligand-NADH can be inhibited by a protein that specifically binds to the ligand. As ATP can be measured in very low concentrations with firefly luciferase, ligands have been labelled with this cofactor.

Drugs may also be monitored using the enzyme-multiplied immunoassay technique by using the NADH-dependent bacterial luminescence system, because in many cases the enzyme label (E) used is an oxidoreductase, e.g. a dehydrogenase.

An assay for amidase activity of α-chymotrypsin may use Boc- and Z-alanylalanylphenylalanamido-4-aminophthalhydrazide. This synthetic substrate releases isoluminol when hydrolyzed by the enzyme. Isoluminol production is determined by measuring its chemiluminescence.

The chemiluminescent system may include at least one chemiluminescent compound and a catalyst, e.g. a ferric ($Fe^{+3}$) ion, hemoglobin, hematin, or products derived from microperoxidase.

The oxidant-responsive chemiluminescent system can further comprise a buffer effective to provide a pH of from about 8.5 to about 12.5. Use of a barbital buffer results in a pH of about 8.5.

The method and apparatus of aspects of this invention may be modified to detect the presence of ozone, ozone and ethylene, or ozone and nitric oxide in air. Therefore, the chemiluminescent reaction may take place between ozone and the organic dye commonly referred to as Rhodamine B.

The luminescent reactions (e.g., ozone/Rhodamine B) are ones wherein luminescence is stimulated and the amount of reactant (ozone) determines the intensity of light given off by the reaction. However, quenching of luminescence is also included within the term "luminescent reaction". The present invention may therefore be modified to be used in conjunction with a material which normally luminesces and which is quenched by the presence of a pollutant. For example, if hydrogen fluoride is a substance to be detected, magnesium oxinate may be used as the luminescent material. The magnesium oxinate normally luminesces when subjected to a 3650 Angstrom black light and the luminescence is quenched in the presence of hydrogen fluoride. Thus, a photographic film subjected to a light emitted from the luminescing magnesium oxinate becomes denser with time of exposure. A filter should be provided to avoid exposure of the film to the 3650 Angstrom black light. When hydrogen fluoride is present, causing a reduction in the light emitted from the luminescing magnesium oxinate, the film will be less dense for a given time of exposure by a measurable amount, thus giving a measurement of the amount of hydrogen fluoride present.

The present invention in its various aspects may be applied in bioluminescent reactions for the assay of substances of clinical interest which are based on reactions involving cofactors, e.g. nicotinamide adenine dinucleotide/reduced form (NAD/NADH) and adensosine triphosphate (ATP).

Several bioluminescent systems are known and the following are examples of some such systems contemplated for use according to the method and apparatus of aspects of the present invention.

In firefly luminescence, the light-producing reaction requires the enzyme luciferase, luciferin, $Mg^{2+}$, ATP, and molecular oxygen. Luciferase is a generic term referring to an enzyme that catalyzes the oxidation of a substrates, such as luciferin, with light emission. Luciferin is a generic term referring to a reduced compound that can be oxidized in an appropriate environment to produce an electronically excited singlet state; light is produced on its return to the ground state.

The initial reaction is the rapid conversion, in the presence of $Mg^{2+}$ and ATP, of luciferin to luciferyl adenylate, which, in the presence of luciferase, combines with molecular oxygen to give an oxyluciferyl adenylate-enzyme complex in the excited state. After emission, the ground-state complex disassociates to form enzyme, adenosine monophosphate (AMP), oxyluciferin, and carbon dioxide, the last being derived from the carboxyl group of luciferin. The reaction is best carried out at about 25° C. in glycine buffer at pH about 7.8. The color of the light emitted differs for different species of firefly, although the structure of luciferin is identical for all species. Intensity and wavelength of maximal emission are also altered by changes in pH, ionic strength, temperature, and the presence of chlorides of $Zn^{2+}$ or $Cd^{2+}$.

The reaction is not specific for ATP; other nucleotides, e.g. cytidine-5'-triphosphate, inosine-5'-triphosphate, and iso-ATP can stimulate light emission. Manganese cations inhibit the reaction ($SCN^- < I^- < NO_3^- - < Br^- < Cl^-$). Anesthetics e.g. procaine and lidocaine are also inhibitors, and this fact has formed the basis of assays.

Two types of luminescent marine bacteria include Beneckea Harveyi (Photobacterium fischeri strain MAV) and Vibrio Fischeri. In vitro, the components required for luminescence are reduced flavin monoculeotide $FMNH_2$ generated from FMN by the oxidation of NADH or NADPH with the aid of FMN reductase, a long-chain aliphatic aldehyde (R—CHO), oxygen, and bacterial luciferase. The total light produced in the reaction is proportional to the amount of each of the substrates ($O_2$—$FMNH_2$, and R—CHO) when they are present in limiting quantities. This is also true of the luciferase because excess $FMNH_2$ is autooxidized so rapidly as compared with the rate of light emission that $FMNH_2$ has been reconverted to FMN by the time the luciferase finishes its catalytic cycle. Thus, like the other reactants, the luciferase only acts once in the in vitro reaction. It is however, capable of turnover on repeated addition of $FMNH_2$. The aldehyde is oxidized to the corresponding carboxylic acid. Only aliphatic aldehydes (R—CHO) with a chain length (R) of eight or more carbon atoms are effective in the reaction.

Microbial luciferase activity is highly specific for $FMNH_2$, but the enzyme also shows weak activity towards other flavins and flavin analogs. Luciferase is particularly sensitive to thiol reagents, e.g. p-chloromercuribenzoic acid and to reagents that react with lysyl, cysteine and histidinyl residues. Volatile anesthetics, riboflavin, and cyanide, and copper, iron, and other heavy metals also inhibit the enzyme.

Flavin mononucleotide reductase (flavin reductase, NAD(P)H dehydrogenase, or NAD(P)H-FMN oxidoreductase) appears to associate in vitro with bacterial luciferase. FMN reductases isolated from Vibrio fischeri and Beneckea harveyi both show appreciable activity in NADH oxidation over a relatively broad pH range, from pH 5 to pH 10. Riboflavin, FAD, and isomers and analogs of FMN may act as substrates for FMN reductase.

The bioluminescent system of the jellyfish Aequorea consists of protein-chromphore complexes (termed "photoproteins"), which react with $Ca^{2+}$ to produce a bluish luminescence, maximum wavelength is 469 nanometers (nm), independent of dissolved oxygen. The photoprotein consists of a species-specific protein in close association with a chromophore component (luciferin), which is oxidized by the protein in the presence of $Ca^{2+}$ to oxyluciferin, with production of light. The spent photoprotein is termed "blue-fluorescent protein". Metal ions other than $Ca^{2+}$ which can catalyze the Aequorea system are $Sr^{2+}$, $Ba^{2+}$, and all of the lanthanides.

In summary, those bioluminescent systems which may be used according to the apparatus and method of aspects of this invention are represented as follows:

This invention in its various aspects allows the production of a permanent photographic record of chemiluminescent reactions, and by its preferred embodiment allows rapid such production by coupling them with instant photography. In its preferred embodiment, the invention provides increased speed, convenience, and sensitivity of detection.

Modified Use of the Apparatus

The present invention in its preferred embodiment thus provides the total elimination of darkroom requirements, resulting in both enhanced speed and simplicity of data acquisition. In addition, the system is easily adapted for use in laboratories with limited space, facilities, and skilled personnel. Indeed, the system is so portable that it can be adopted for field work at test sites, operating theatres, clinics or a doctor's office in rural communities requiring rapid test results from immunodiagnostic kits. In contrast to radioimmunoassays (RIA), the overall operational cost of the system of aspects of the present invention is significantly lower, while maintaining comparable sensitivity. Additionally, the method of aspects of this invention retains the advantages of eliminating the radio-hazard and waste disposal problems inherent in RIA techniques. Therefore, the system of aspects of this invention can be readily "scaled-up" at minimal capital expenditure for simultaneous or sequential testing of large numbers of patient samples. More importantly, the overall sensitivity of light-emission-based immunoassays is greater than that obtainable with chromogen-based immunoassays which detect the formation of a soluble or insoluble coloured end-product. This enhanced sensitivity stems from the ability to control both exposure times and photographic film speeds. The use of photographic film permits prolonged accumulation of light emission from samples. Thus, very low concentrations of antibody-antigen complexes normally undetectable by chromogen-based assays, are still easily visualized by the system of aspects of the present invention. Photographic output in contrast to chromogenic output provides for a permanent record and other desirable features, e.g. record duplication from the photographic negative, quantification by densitometry, prior encoding for large sample sizes and long-term filling.

The preferred embodiment of the apparatus of aspects of this invention is for solid-phase assays. Thus, a small liquid sample is first absorbed onto membranous matrix (e.g. nitrocellulose), air-dried, and kept for subsequent analysis.

The apparatus of embodiments of this invention ensures that all chemical procedures involved with preparation of the sample (e.g. addition of reactants, washing, etc.) are conducted externally to the detection device. Consequently, the apparatus of aspects of the present invention eliminates the need for a light-proof closure (e.g. a septum) through which reactants are added via a cannula.

The apparatus of embodiments of this invention may be either qualitative or comparative in application. Specifically, the use of the method of an aspect of the present invention may determine the presence or absence of the analyte in question. The objective there would be to detect the presence of the analyte in as low a concentration as possible. In order to maximize detection of luminescence when the analyte is at a very low concentration, the apparatus of an embodiment of the present invention, designed for contact photography, ensures that light is maximally concentrated on the imaging layer and is not allowed to diffuse laterally. The present invention achieves the objective of maximal analytical sensitivity. The apparatus of embodiments of the present invention should find increasing application in the design of clinical immunodiagnositic kits. For example, large scale, qualitative screening for AIDS antibodies requires a maximally sensitive, yet simple, and inexpensive device. The apparatus of aspects of the present invention minimizes the occurrence of false negatives (i.e. presence of antibodies at an analytically undetectable concentration). Once antibodies are qualitatively detected, then more sophisticated, expensive and time-consuming methodologies, (e.g. radio-immunoassay) can be used to quantitate their levels.

Compared with radioimmunoassay, luminescent immunoassay (LIA) has many of the advantages associated with enzyme immunoassay, i.e. (1) the reagents are cheap and stable, (2) assays are rapid, (3) radiation hazards are obviated, and, in addition, these methods offer the added advantage of very sensitive detection.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. Apparatus for the detection of a chemiluminescent reaction and for the production of a permanent photographic record of such chemiluminescent reaction, comprising:

(A) a first element comprising:
(a) a sample holder including clamp means to hold a test sample in a transparent container in selected positions;
and (b) holding means to hold said clamp means in a first position of said selected positions, where said transparent container containing said test sample is out of contact with said photographic film supply, and to release said clamp means to a second position of said selected positions, where said transparent container containing said test sample is in direct contact with said photographic film supply;

(B) a second element comprising:
(c) a supply of photographic film sensitive to chemiluminescence;
and (d) a shutter means to enable a source of chemiluminescence directly to contact a selected unit of said photographic film;

and (C) a third element comprising:
(e) an adaptor to provide a light-tight union between said first element (A) and said second element (B), said adaptor including a central window through which said sample holder projects; whereby, upon manual actuation of said holding means to release said sample clamp means said sample holder is dropped, thereby to place said container containing said test sample into direct contact with said selected unit of photographic film.

2. The apparatus of claim 1 wherein said element (B) comprises a box holding a plurality of units of prepackaged, instant-developing photographic film.

3. The apparatus of claim 2 wherein said shutter means comprises a sliding shtter which is manually actuatable to provide a central open window to permit said holding means to drop said sample holder to place said container containing said test sample into direct contact with a selected unit of said photographic film.

4. The apparatus of claim 1 wherein said sample clamp comprises a box having an open bottom floor, and includes means to hold said test sample in said container therein.

5. The apparatus of claim 4 wherein said test sample in said container is in the form of a sample sheet absorbed with said test sample and protected within a transparent sample container.

6. The apparatus of claim 5 wherein said sample sheet comprises a nitrocellulose membrane having luminescent analyte absorbed thereon.

7. The apparatus of claim 4 wherein said test sample in said container is in the form of a plurality of well plates or tubes containing liquid luminescent analyte.

8. The apparatus of claim 4 wherein the inner face of said sample clamp means is provided with a light-reflective surface.

9. The apparatus of claim 4 wherein said sample clamp is held to said sample holder by a lockable position adjuster against the urging of spring means.

10. The apparatus of claim 9 wherein said spring means comprises a leaf spring.

11. The apparatus of claim 9 wherein said position adjuster is adapted to be unlocked to release said sample clamp means to allow said sample holder to be positively urged downwardly by said spring means.

12. The apparatus of claim 1 wherein said third element (C) is of the type including cooperating tongues-and-grooves, or hinges and clamps.

13. Apparatus for producing a permanent photographic record of a chemiluminescent reaction of a sample comprising:
film holder means for holding a photographic film sensitive to a chemiluminescent reaction of said sample, said film holder means defining a window in registry with any photographic film which may be held in said film holder means;
sample holding means for holding said sample in registry with said window and any photographic film which may be held in said film holder means, and for allowing movements of said sample relative to any photographic film which may be held in said film holder means between (i) a raised position, wherein said sample holding means, and thus said sample is in spaced relation to any photographic film which may be held in said film holder means and (ii) a lowered position, wherein said sample holding means is in sufficiently close proximity to any photographic film which may be held in said film holder means to allow said sample held thereby directly to contact any photographic film which may be held in said film holder means; and
shutter means operatively associated with said window of said film holder means and movable between a closed position, wherein said shutter means obstructs said window so as to prevent said sample holding means from moving into sad lowered position, and an opened position, wherein said window is unobstructed by said shutter means so as to permit said sample holding means to move from said raised position to said lowered position.

14. The apparatus of claim 13 including photographic film held in said film holder means.

15. The apparatus of claim 14 wherein said film is instant developing film.

16. The apparatus of claim 13, wherein said sample holding means includes sample clamp means for releasably holding said sample holding means in said raised position.

17. The apparatus of claim 16 wherein said sample clamp comprises a box having an open bottom floor, and includes means to hold said test sample in said container therein.

18. The apparatus of claim 13 wherein said test sample in said container is in the form of a sample sheet absorbed with said test sample and protected within a transparent sample container.

19. The apparatus of claim 18 wherein said sample sheet comprises a nitrocellulose membrane having luminescent analyte absorbed thereon.

20. The apparatus of claim 13 wherein said test sample in said container is in the form of a plurality of well plates or tubes containing liquid luminescent analyte.

21. The apparatus of claim 13 wherein the inner face of said sample clamp means is provided with a light-reflective surface.

22. The apparatus of claim 21 wherein said sample clamp is held to said sample holder by a lockable position adjuster against the urging of spring means.

23. The apparatus of claim 22 wherein said spring means comprises a leaf spring.

24. The apparatus of claim 22 wherein said position adjuster is adapted to be unlocked to release said sample clamp means to allow said sample holder to be positively urged downwardly by said spring means.

25. The apparatus of claim 13 including means providing a light-tight union between such film holder means and said sample holding means.

* * * * *